US010968322B2

(12) United States Patent
Satlewal et al.

(10) Patent No.: US 10,968,322 B2
(45) Date of Patent: Apr. 6, 2021

(54) METHOD FOR IMPROVED PRODUCTION OF FERMENTABLE SUGARS FROM LIGNOCELLULOSIC BIOMASS USING ADDITIVE AND ENZYME

(71) Applicants: INDIAN OIL CORPORATION LIMITED, Mumbai (IN); DEPARTMENT OF BIOTECHNOLOGY, New Delhi (IN)

(72) Inventors: Alok Satlewal, Faridabad (IN); Ruchi Agrawal, Faridabad (IN); Ravindra Kumar, Faridabad (IN); Anshu Shanker Mathur, Faridabad (IN); Ravi Prakash Gupta, Faridabad (IN); Biswajit Basu, Faridabad (IN); Deepak Kumar Tuli, Faridabad (IN)

(73) Assignees: INDIAN OIL CORPORATION LIMITED, Mumbai (IN); DEPARTMENT OF BIOTECHNOLOGY, New Delhi (IN)

( * ) Notice: Subject to any disclaimer, the term of this patent is extended or adjusted under 35 U.S.C. 154(b) by 162 days.

(21) Appl. No.: 16/271,423

(22) Filed: Feb. 8, 2019

(65) Prior Publication Data

US 2019/0248962 A1 Aug. 15, 2019

(30) Foreign Application Priority Data

Feb. 9, 2018 (IN) .............................. 201821005003

(51) Int. Cl.
| | |
|---|---|
| *C08H 8/00* | (2010.01) |
| *C12P 19/02* | (2006.01) |
| *C12P 19/12* | (2006.01) |
| *D21C 5/00* | (2006.01) |
| *D21B 1/16* | (2006.01) |
| *D21C 3/04* | (2006.01) |

(52) U.S. Cl.
CPC ................ *C08H 8/00* (2013.01); *C12P 19/02* (2013.01); *C12P 19/12* (2013.01); *D21B 1/16* (2013.01); *D21C 3/04* (2013.01); *D21C 5/005* (2013.01); *C12P 2201/00* (2013.01)

(58) Field of Classification Search
CPC .. A61P 17/00; A61P 17/04; A61P 1/00; A61P 1/04; A61P 29/00; A61P 43/00; B01J 2219/00592; B01J 2219/00695; C07B 2200/11; C07F 9/143; C07F 9/2408; C07F 9/2429; C07F 9/572; C07F 9/5728; C07F 9/59; C07F 9/65031; C07F 9/65038; C07F 9/6506; C07F 9/6512; C07F 9/6521; C07F 9/6533; C07F 9/65335; C07F 9/6547; C07F 9/6561; C07F 9/65616; C07H 21/00; C07H 17/02; C07H 1/06; C07H 1/08; C12P 19/02; C12P 19/12; C12P 2201/00; C12P 13/02; C12P 19/04; C12P 19/14; C08H 8/00; D21B 1/16; D21B 1/30; A61K 45/06; C07D 237/00; D21C 3/04; D21C 5/005; D21C 1/02
See application file for complete search history.

(56) References Cited

U.S. PATENT DOCUMENTS

| | | | |
|---|---|---|---|
| 7,354,743 B2 | 4/2008 | Vlasenko et al. | |
| 2008/0299613 A1* | 12/2008 | Merino | C07K 14/37 435/69.1 |
| 2010/0124770 A1 | 5/2010 | Sabesan et al. | |
| 2010/0291650 A1 | 11/2010 | Larsen et al. | |
| 2017/0211231 A1* | 7/2017 | Baker | D21C 3/20 |

FOREIGN PATENT DOCUMENTS

| | | |
|---|---|---|
| WO | 2008/134037 A1 | 11/2008 |
| WO | 2013/083816 A1 | 6/2013 |

\* cited by examiner

*Primary Examiner* — Deborah K Ware
(74) *Attorney, Agent, or Firm* — Maschoff Brennan

(57) ABSTRACT

The present invention relates to an additive or additive composition for improved production of fermentable sugars from lignocellulosic biomass during enzymatic hydrolysis. More particularly, the present invention discloses petrochemical waste as an additive or an additive composition containing one or more ethylene glycol oligomers and one or more metal ions which are useful for improved production of fermentable sugars from lignocellulosic biomass during enzymatic hydrolysis.

7 Claims, 13 Drawing Sheets

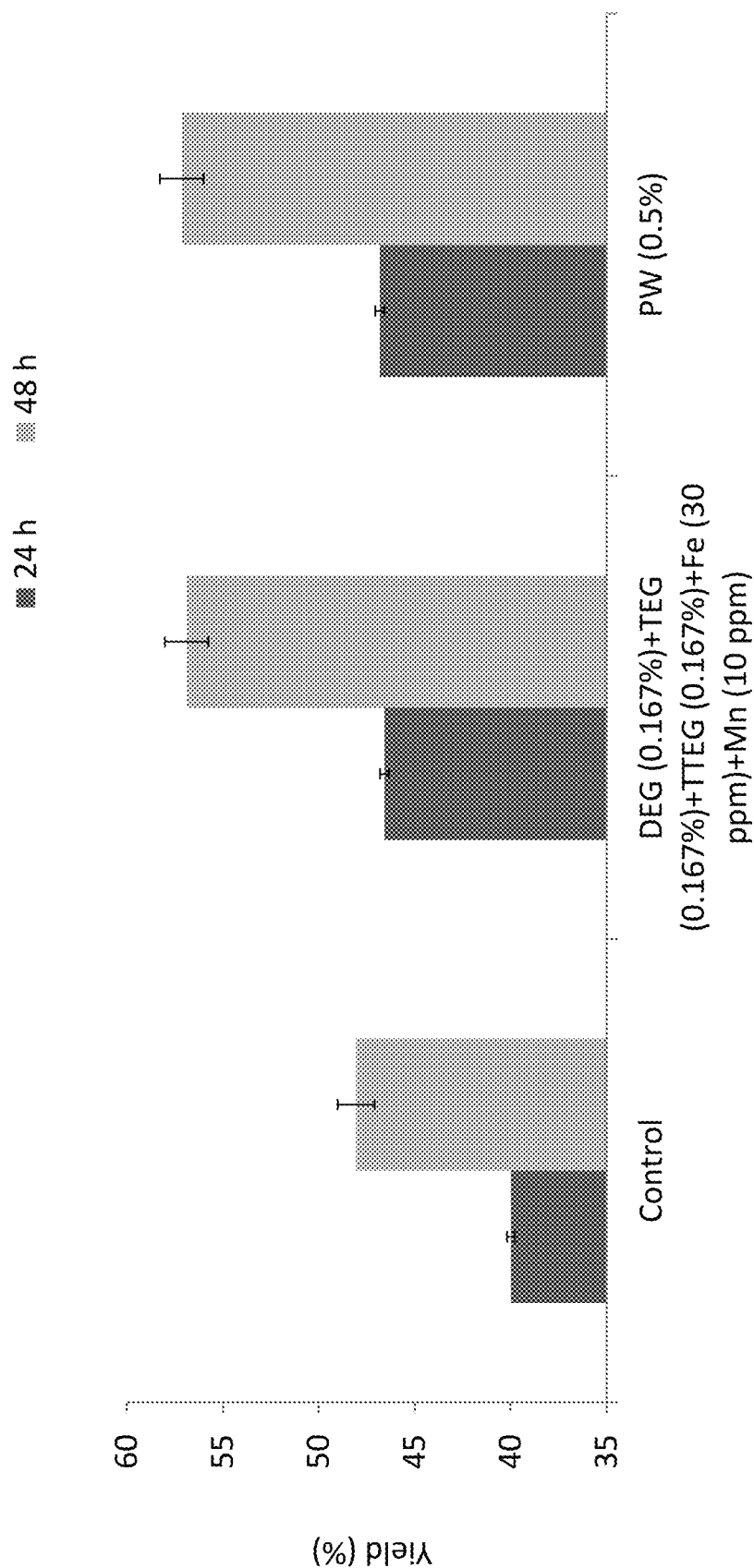

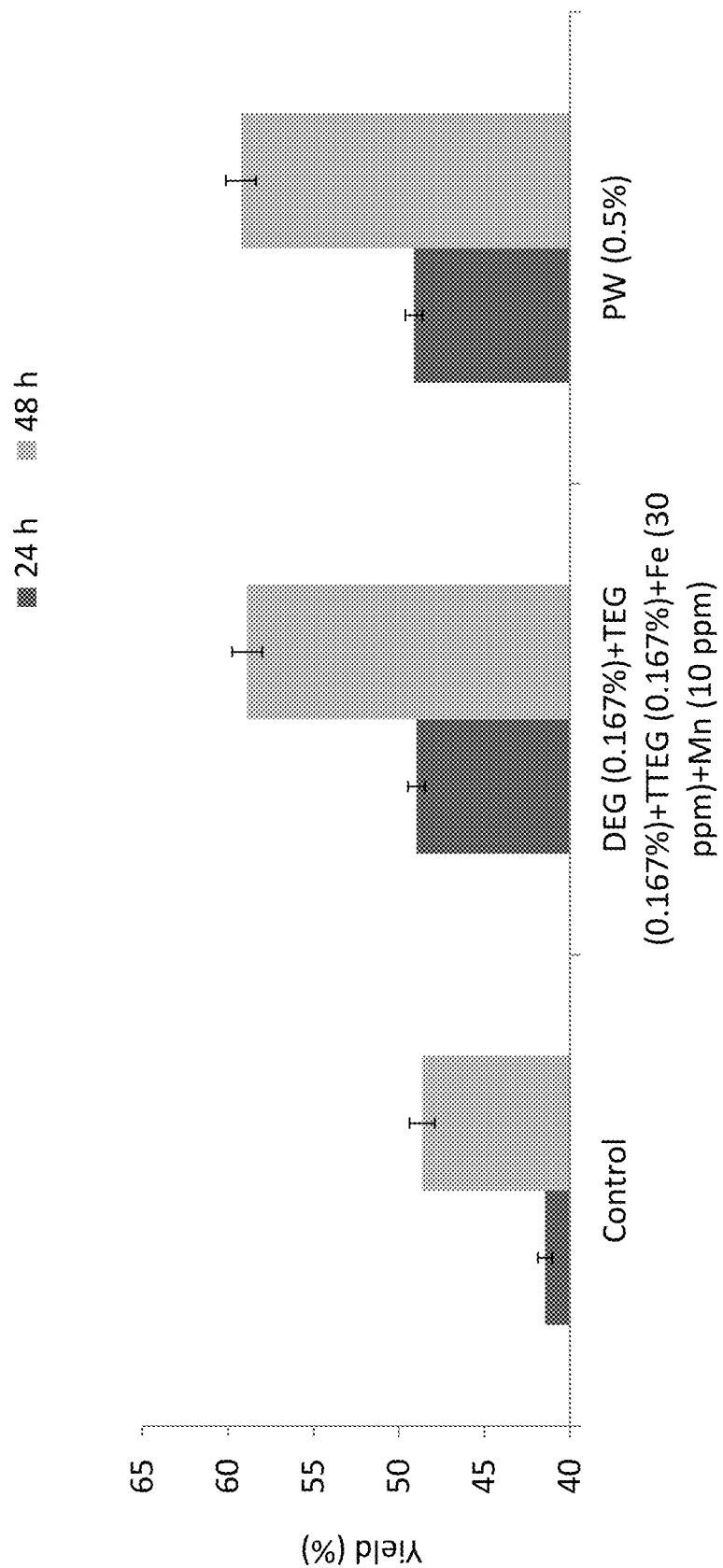

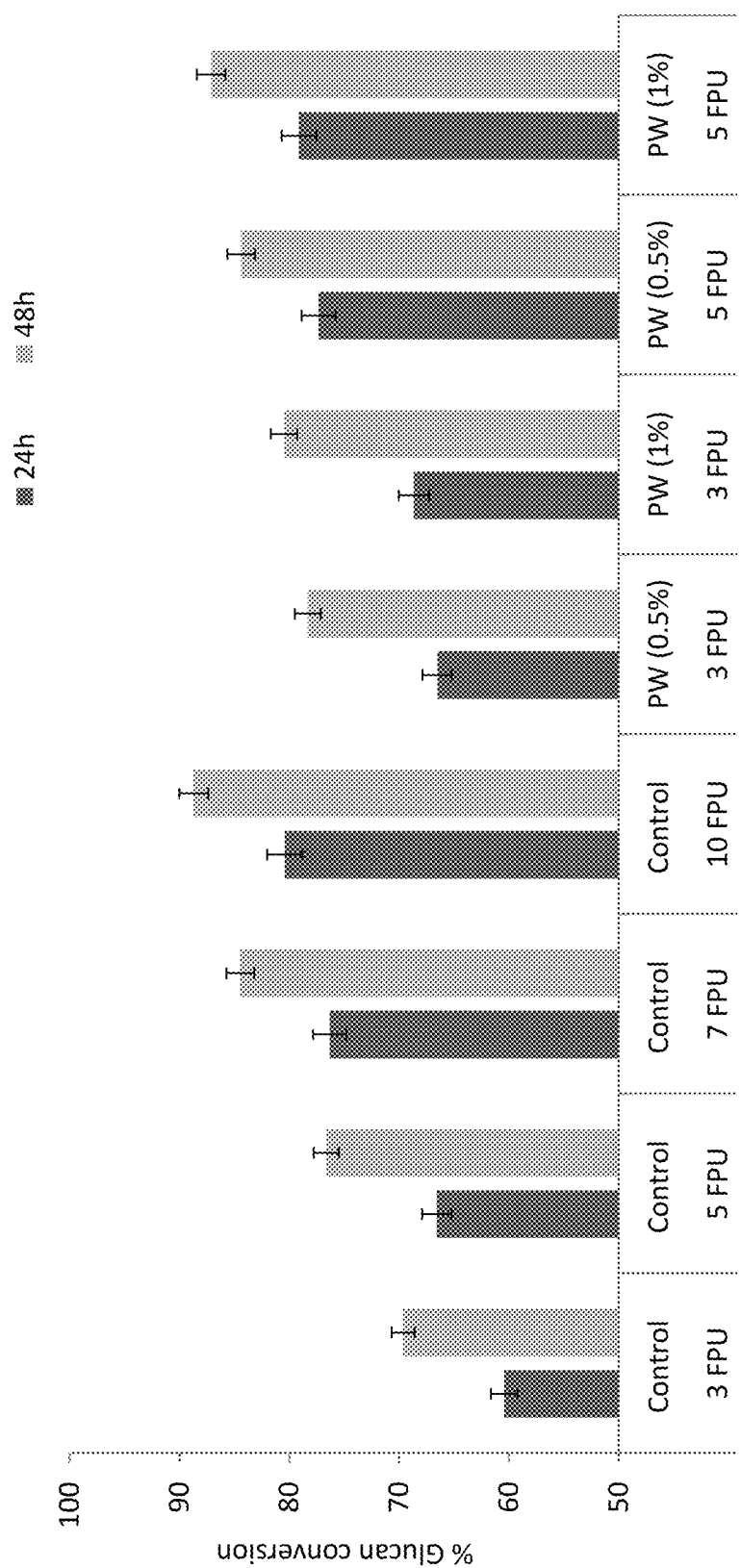

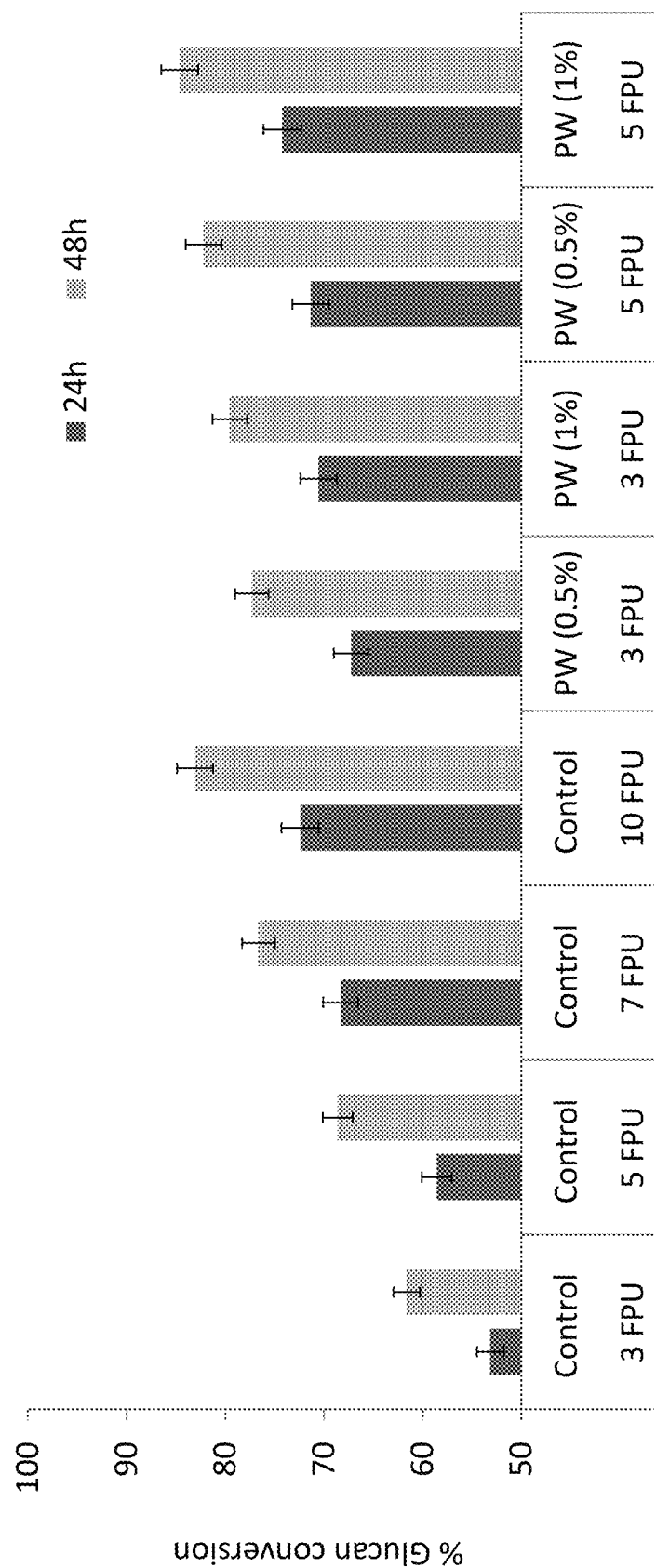

US 10,968,322 B2

METHOD FOR IMPROVED PRODUCTION OF FERMENTABLE SUGARS FROM LIGNOCELLULOSIC BIOMASS USING ADDITIVE AND ENZYME

FIELD OF THE INVENTION

The present invention discloses an additive composition useful for improved production of fermentable sugars from lignocellulosic biomass during enzymatic hydrolysis. More particularly, the present invention discloses petrochemical waste as an additive or an additive composition containing ethylene glycol oligomers and metal ions which are useful for improved production of fermentable sugars from lignocellulosic biomass during enzymatic hydrolysis.

BACKGROUND OF THE INVENTION

Biofuel from lignocellulosic biomass is a promising alternative approach for meeting the global energy needs. Pretreatment, enzymatic hydrolysis and fermentation are three integral parts of this process. Pretreatment is required to open up the biomass structure so that the cellulolytic enzymes can access the holocellulose and convert it into monomeric sugars. Following this fermentation is carried out to produce ethanol by using fermenting yeast or bacteria.

High cost of enzymatic hydrolysis of pretreated biomass is a major challenge affecting the ethanol cost. It has been realized that lignin present in pretreated lignocellulosic biomass binds non-productively with enzymes and inhibits hydrolysis efficiency. Lignin also provides stearic hindrance and this limits the enzyme accessibility to substrate. Therefore, high enzyme concentrations are required to achieve optimal holocellulose conversion.

Lignocellulose is ubiquitous in all wood species and all agricultural and forestry waste. In addition, municipal waste, which typically contains about half waste paper and yard waste, is a source of lignocellulosic materials. Currently, municipal waste is buried or burned at considerable expense to the disposer or the government organization providing solid waste services.

WO 2013/083816 A1 describes a process wherein the pretreatment process is carried out in the presence of a tertiary polyamide additive to improve the efficiency of the hydrolysis process for the generation of sugar from lignocellulosic biomas.

US 2010/0291650 A1 describes a process where the addition of PEG or surfactant enhanced the cellulase hydrolysis yields and reduced the cellulase enzyme consumption.

US 2010/0124770A1 describes a process for obtaining concentrated sugar solution from polysaccharide enriched biomass by adding at least one additive selected from the group consisting of polyethylene glycols, fatty acid esters, fatty acid ethoxylates, non-ionic surfactants derived from polyethoxylated sorbitan and a fatty acid, sodium laurimi-nodipropionate, sodium cocoamphoacetate, sodium tridecyl ether sulfate and a combination of these, such that enzyme loading of the hydrolysis enzyme consortium can be reduced.

WO 2008/134037 A1 describes a method to enhance the enzymatic digestibility of pretreated corn stover by adding surfactants at 160-220° C. with and without acid.

U.S. Pat. No. 7,354,743 B2 describes a method for degrading the lignocellulosic material with an effective amount of one or more cellulolytic enzymes in the presence of at least one surfactant selected from the group consisting of a secondary alcohol ethoxylate, fatty alcohol ethoxylate, nonylphenol ethoxylate, tridecyl ethoxylate, and polyoxyethylene ether, wherein the presence of the surfactant increases the degradation of lignocellulosic material compared to the absence of the surfactant.

The above mentioned methods are applicable to hydrolysis at very low solid loadings (i.e., 1% to 5%) of dilute acid pretreated biomass using cellulolytic enzymes in the presence of high concentrations of pure and expensive surfactants (more than 2.5-15% of biomass).

Further, it is well-known in prior-art documents that there is increase in hydrolysis with increase in enzyme dosage. However, yield of said hydrolysis did not increase in linear fashion with increasing enzyme dosage.

Therefore, there exists an unmet need of any additive or additive composition which provides increase in yield of biomass hydrolysis in linear fashion without much increase in enzyme dosage and without using expensive surfactants.

The present invention addresses such problems existing in the art in an economic and effective way.

The present invention discloses an additive composition useful for improved production of fermentable sugars from lignocellulosic biomass, wherein the additive comprising ethylene glycol oligomers and metals which act in a synergistic manner. More particularly, the present invention also discloses use of petrochemical waste as additive or additive composition containing said ethylene glycol oligomers and metal ions useful for improved production of fermentable sugars from lignocellulosic biomass.

OBJECTS OF THE INVENTION

An object of the present invention is to provide improved production of fermentable sugars from lignocellulosic biomass.

Another object of the present invention is to provide an additive or an additive composition comprising ethylene glycol oligomers, i.e., diethylene glycol (DEG), triethylene glycol (TEG), tetraethylene glycol (TTEG) and metals such as Iron (Fe) and Manganese (Mn) for improved production of fermentable sugars from lignocellulosic biomass.

Still another object of the present invention is to use petrochemical waste as additive or additive composition containing said ethylene glycol oligomers and metal ions useful for improved production of fermentable sugars from lignocellulosic biomass.

Still another object of the present invention is to use petrochemical waste as additive or additive composition so as to require less dosage of enzyme for production of fermentable sugars from lignocellulosic biomass.

SUMMARY OF THE INVENTION

In a feature of the present invention, the present invention discloses a method for production of fermentable sugars from lignocellulosic biomass, comprising: a) feeding a grounded lignocellulosic biomass feedstock into a pretreatment reactor system for dilute acid impregnation at room temperature or at a temperature ranging from 50-100° C. for a period 5-60 minutes to render it acid-soaked; b) removing 40%-70% acid from said acid-soaked biomass by pressing in a hydraulic press; c) feeding said pressed biomass to a plug mill using feed hopper with feed rate of 8-12 kg/hour for conversion of biomass material into solid plug(s); d) treating said solid plugs with dilute acid in an amount of 0.02 to 3% w/w of the biomass having pH 1-3 at 120-200° C. for a residence time in the range of 8-12 minutes for conversion into biomass slurry; e) centrifuging said biomass slurry for separating solids and liquids, followed by washing solid mass to a pH of 7.0; and f) hydrolyzing said acid pretreated solid biomass with an additive and enzyme for 40-50 hours in an incubator shaker at 45-55° C. having speed of 180-220 rpm to obtain fermentable sugars.

In another feature of the present invention, the acid used in the pretreatment step is selected from the group consisting of sulphuric acid, hydrochloric acid, acetic acid and phosphoric acid.

In another feature of the present invention, the acid used is in diluted form.

In another feature of the present invention, the dilute acid added to the lignocellulosic biomass in step a) is in an amount of 0.02 to 3% w/w of the biomass.

In another feature of the present invention, the additive is a petrochemical waste.

In another feature of the present invention, the petrochemical waste comprising one or more ethylene glycol oligomer(s) and one or more metal(s).

In another feature of the present invention, the ethylene glycol oligomer is selected from the group consisting of monoethylene glycol (MEG) present in an amount ranging from 0.0-0.5%, diethylene glycol (DEG) present in an amount ranging from 0.5-30.0%, triethylene glycol (TEG) present in an amount ranging from 40.0-50.0%, and tetraethylene glycol (TTEG) present in an amount ranging from 25-50%.

In another feature of the present invention, the metal is selected form the group comprising of iron (Fe) in an amount of 0.58%, sodium (Na) in an amount of 0.02%, Chromium (Cr) in an amount of 0.015%, Boron (B) in an amount of 0.012% and manganese (Mn) in an amount of 0.0078%.

In another feature of the present invention, the petrochemical waste is used for production of fermentable sugars from lignocellulosic biomass.

BRIEF DESCRIPTION OF THE ACCOMPANYING FIGURES

The reference will now be made to exemplary embodiments so that the disclosure may be readily understood and put into practical effect. It will be illustrated with reference to the accompanying figures. The figures together with a detailed description below, are incorporated in and form part of the specification, and serve to illustrate the embodiments further and explain various principles and advantages, in accordance with the present disclosure wherein.

Figure 3:
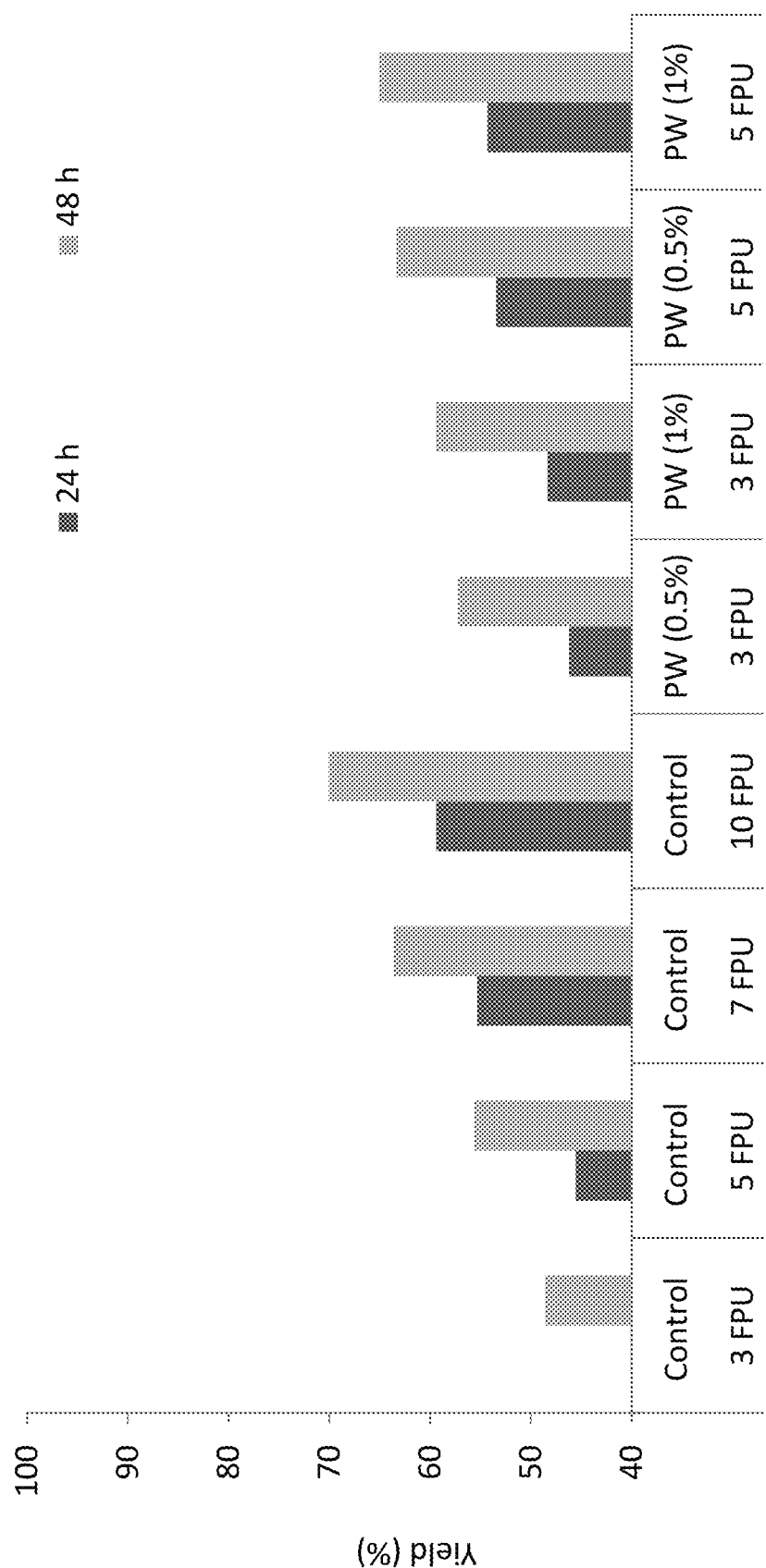

FIG. 3 shows hydrolysis of dilute acid pretreated wheat straw (DAWS) with 0.5% and 1% petrochemical waste stream (PW) at enzyme dosage of 3-10 FPU/g of biomass and 10% solid loadings.

Figure 4:
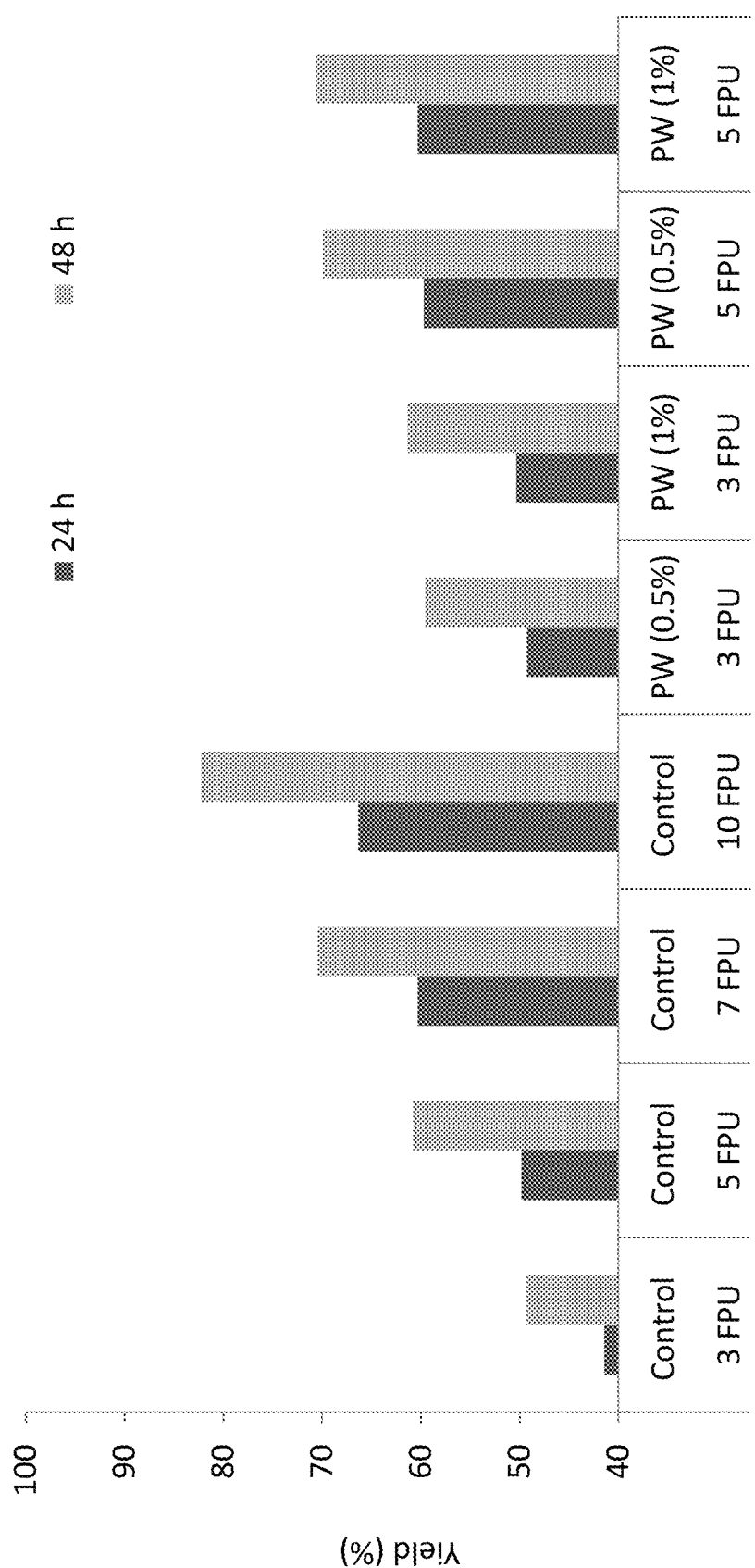

FIG. 4 shows hydrolysis of steam pretreated wheat straw (SEWS) with 0.5% and 1% petrochemical waste stream (PW) at 3-10 FPU enzyme dosage and 10% solid loadings.

Figure 5:
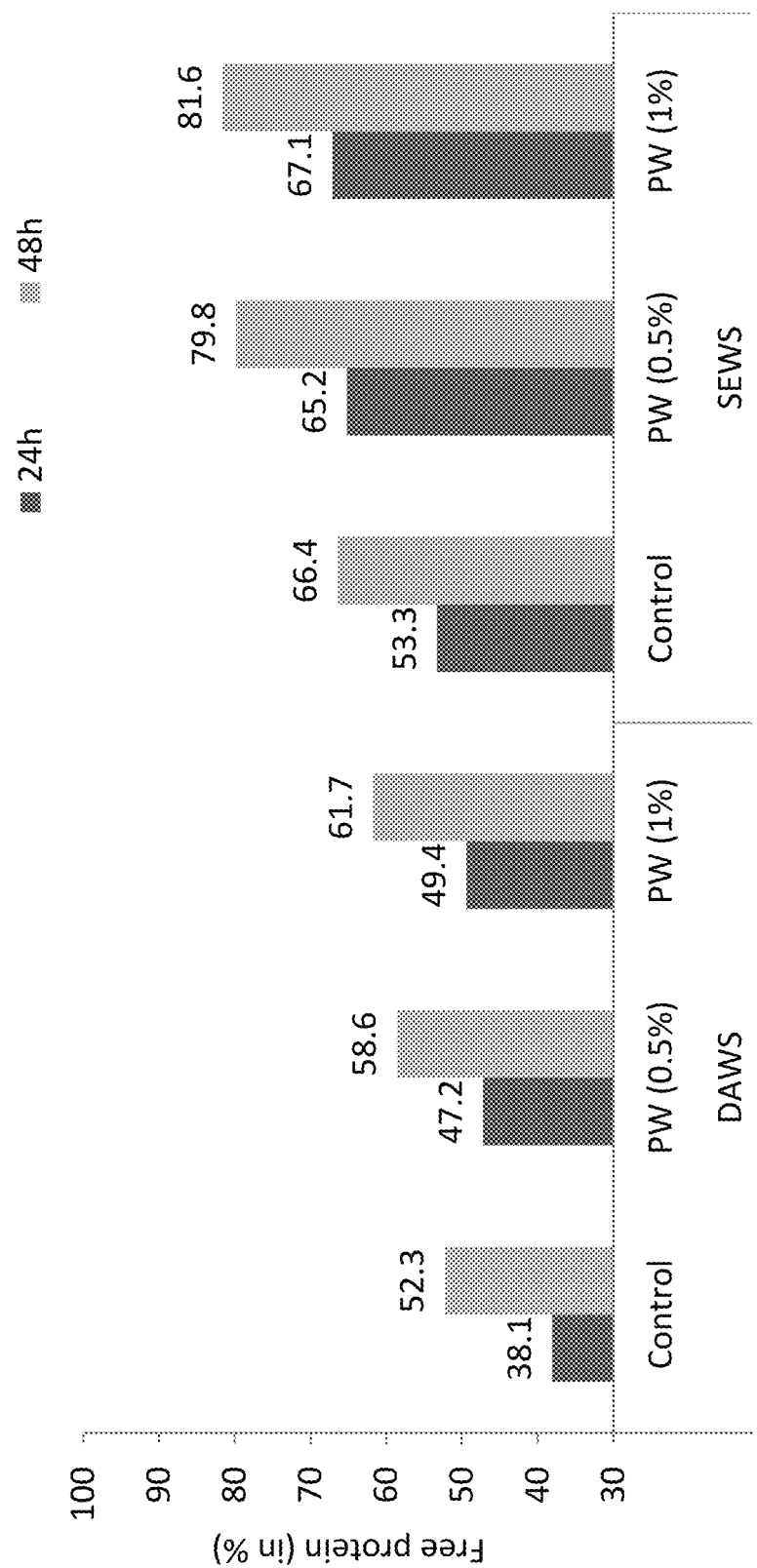

FIG. 5 shows free Protein (%) during hydrolysis of DAWS and SEWS with and without 0.5% and 1% petrochemical waste stream (PW) at 3 FPU enzyme dosage and 10% solid loadings.

FIGS. 6(a)-6(f) show comparative evaluation of PW and its constituents individually or in combinations during hydrolysis of: (a)-(c) dilute acid (DAWS) and (d)-(f) steam pretreated (SEWS) wheat straw.

FIGS. 7(a)-7(b) show hydrolysis of pretreated rice straw (RS) with 0.5% and 1% petrochemical waste stream (PW) at 3-10 FPU enzyme dosage.

DETAILED DESCRIPTION OF THE INVENTION

The present invention discloses an additive composition useful for improved production of fermentable sugars from lignocellulosic biomass. The present invention also discloses an additive comprising ethylene glycol oligomers, i.e., monoethylene glycol (MEG), diethylene glycol (DEG), triethylene glycol (TEG), tetraethylene glycol (TTEG) and metals Iron (Fe) and Manganese (Mn) which act in a synergistic manner and improve the enzymatic hydrolysis. Further, the present invention also discloses a petrochemical waste containing above metal ions and ethylene glycol oligomers useful for improved production of fermentable sugars from lignocellulosic biomass.

In an embodiment of the present invention, an additive composition useful for improved production of fermentable sugars from lignocellulosic biomass comprising: MEG (0-0.5%), DEG (0.5-30%), TEG (40-50%), TTEG (25-50%), other higher molecular weight ethylene glycols, i.e., pentamers to dodecamers (1.3%) and metals salts. Iron (Fe) is present at a concentration of 5842 ppm (0.58%) followed by sodium (Na) at 200 ppm (0.02%), Chromium (Cr) at 150 ppm (0.015%), Boron (B) at 112 ppm (0.012%), manganese (Mn) at 78 ppm (0.0078%) and others (Ag, Al, As, Ba, Be, Bi, Ca, Cd, Co, Cu, K, Li, Mg, Mo, Ni, Pb, Sb, Ti, V, Zn, Si, P) at concentrations <10 ppm.

In accordance with the present invention, a method is provided wherein an improved production of fermentable sugars from lignocellulosic biomass by utilizing the additive composition as disclosed herein is used as an additive during enzymatic hydrolysis. Further, a method for improved production of fermentable sugars from lignocellulosic biomass is disclosed, comprising of the following steps:
1. Dilute acid pretreatment of lignocellulosic biomass;
2. Enzymatic hydrolysis with additive composition.

In an embodiment of the present invention, the biomass may be used directly as obtained from the source, or may be subjected to some preprocessing. In another embodiment of the present invention, one or more pretreatment step may precede the dilute acid pretreatment step. In yet another embodiment, petrochemical waste containing above metal ions and ethylene glycol oligomers may be used directly as additive during enzymatic hydrolysis.

In accordance with the present invention, the lignocellulosic biomass herein includes, but is not limited to, bioenergy crops, agricultural residues, wood and forestry waste like trees, branches, roots, leaves, wood chips, sawdust, and other like materials. In another embodiment, biomass that is useful for the invention has a relatively high carbohydrate content, is relatively dense, and/or is relatively easy to collect, transport, store and/or handle. In another embodiment of the invention, biomass that is useful includes corn cobs, corn stover, sugar cane bagasse, sugar cane straw, rice straw, cotton stalk, Jatropha cuttings and switchgrass. The lignocellulosic biomass may be derived from a single source, or can comprise a mixture derived from more than one source.

In accordance with the present invention, during the dilute acid pretreatment, the concentration of the acid added to the lignocellulosic feedstock may be between about 0.02 to about 3% w/w of biomass and the acid pretreatment may be carried out for about 5 min to 60 min. The acid soaking in the acid pretreatment step may be carried out at room treatment or at temperature ranging from 50° C. to 100° C. In accordance with the present invention, the temperature of the pretreatment is between about 120° C. and about 200° C. The pretreatment temperature utilized in the process will depend on the retention time, acid concentration and the feedstock used. The pretreatment conditions are applied so as to hydrolyze 40%-90% hemicellulose (xylan, arabinan etc.) in to sugars and to obtain minimum amount of inhibitors like furfurals, hydroxy methyl furfural, levulinic, acetic acids, formic acid etc.

In accordance with the present invention, after pretreatment, slurry is cooled prior to enzymatic hydrolysis so that the enzymatic hydrolysis could be carried out at desired temperature range of 45° C.-55° C. The whole slurry or filtered and/or washed solids could be taken up in a hydrolysis reactor for subsequent hydrolysis in to monomers. In an embodiment of the present invention, a complex of secreted enzymes from filamentous fungi (particularly *Trichoderma* sp.) is used for pretreated biomass hydrolysis.

In accordance with the present invention, the ethylene glycol oligomers are also referred as surfactant in the present application.

Having described the basic aspects of the present invention, the following non-limiting examples illustrate specific embodiment thereof.

Example 1

Example 1.1: Dilute Acid Pretreatment of Wheat Straw

Figure 1:
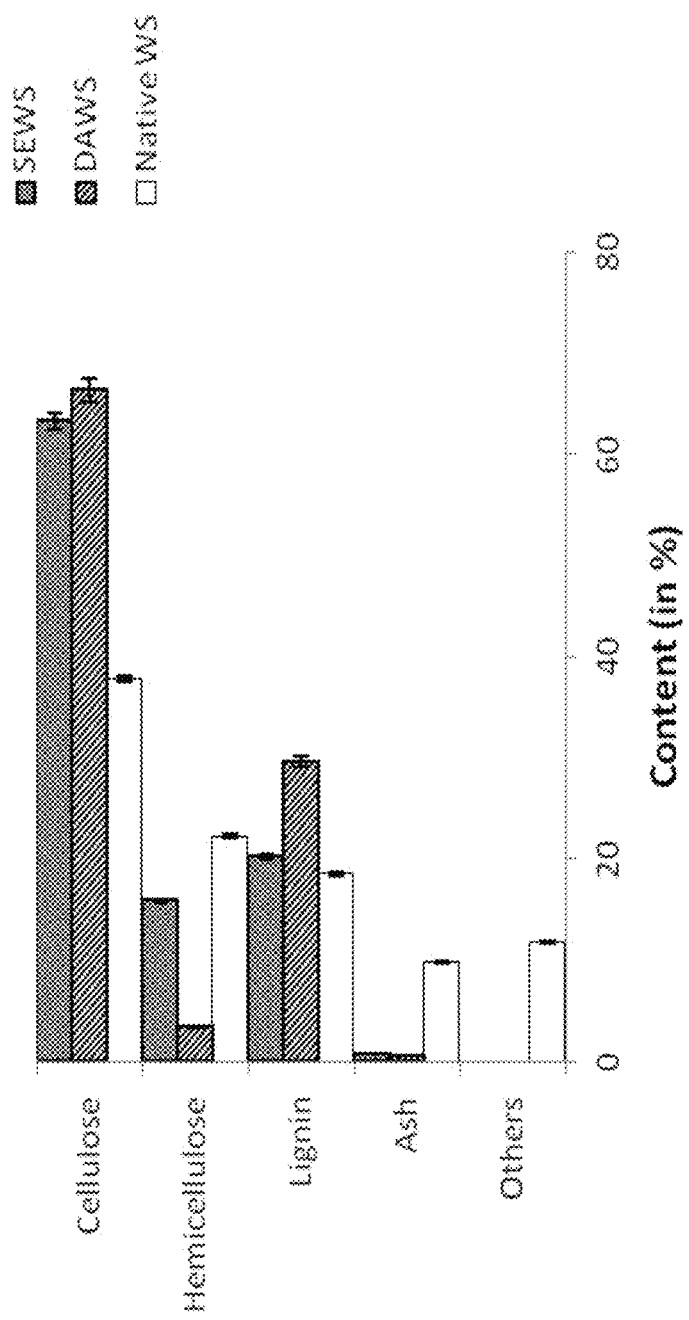
FIG. 1 illustrates composition of native wheat straw, dilute acid treated wheat straw (DAWS) and steam exploded wheat straw (SEWS).

Native wheat straw (WS) was procured from local market in Faridabad, Haryana, India and grounded in to 1-2 mm size. A 250 kg/day continuous pilot-scale pretreatment reactor system was used for wheat straw (WS) pretreatment using dilute sulfuric acid. It includes a size reduction mill, high temperature and pressure reactor, flash tank, hydraulic press and a weight loss type feed hopper. The milled WS was presoaked in the acid solution for 30 minutes followed by pressing in a hydraulic press to remove excess liquid. The pressed WS was fed to the feed hopper, which maintains the desired feed rate of 10 kg/h. The material exits through a conveyor belt that delivers it to a plug mill that compresses the material into a strong solid plug that is then pushed into the pretreatment reactor. This unique arrangement helps to maintain the steam pressure in the reactor while continually injecting the feed into the reactor. After passing through the screw type pretreatment reactor, the pretreated material reaches to a flash tank. Pretreatment was carried out at 160° C. temperature, 10 min residence time and 0.5% (v/v) sulfuric acid. The pretreated biomass slurry (containing cellulose, hemicelluloses and lignin) was collected in the slurry tank. The pretreated wheat straw slurry (containing cellulose, hemicelluloses and lignin) was collected in the slurry tank and transferred through a pump to a high speed centrifuge (at 5000 rpm for 10 min) for separating solids (mainly cellulose and lignin) and liquid (mainly pentoses). The separated solids were then repeatedly washed with water to a pH of 7.0 stored at −20° C. The chemical composition of dilute acid pretreated wheat straw (DAWS) was analyzed by NREL protocol (NREL/TP-510-42618) and is given in FIG. 1 along with native wheat straw.

Example 1.2: Steam Explosion Pretreatment of Wheat Straw

Impregnation of WS was carried out in batches of 15 kg by placing it in a stainless steel (SS) wire mesh bin by dipping into water. The liquid was circulated using a pneumatic pump for each experiment for 30 min at room temperature (30° C.). The soaked wheat straw was dewatered using hydraulic press at a pressure of 100 bars. The pressed wheat straw was properly mixed to determine moisture content using moisture analyzer (MA 150 Sartorius, Germany). Steam explosion digester was designed in-house, comprising of high pressure reactor of 10 L (SS) equipped with feeding device, cyclone separator, quick opening pneumatic butterfly valve and noise absorber. Before starting the experiment, steam explosion digester was flushed 3-4 times with a pressure (10 bar) to quickly attain the desired operation temperature. 0.4 kg of pressed wheat straw on dry basis was subjected to the digester and temperature was increased by injecting of high pressure steam (15 bar). The WS was pretreated at 200° C. temperature for a reaction time of 10 min. After pretreatment, the wheat straw slurry was recovered from cyclone separator, and separated into two fractions, xylose rich liquid hydrolysate and glucan rich solid residue. The chemical composition of steam pretreated wheat straw (SEWS) was analyzed by NREL protocol (NREL/TP-510-42618) and is given in FIG. 1 along with native wheat straw.

Example 1.3: Dilute Acid Pretreatment of Rice Straw

Figure 2:
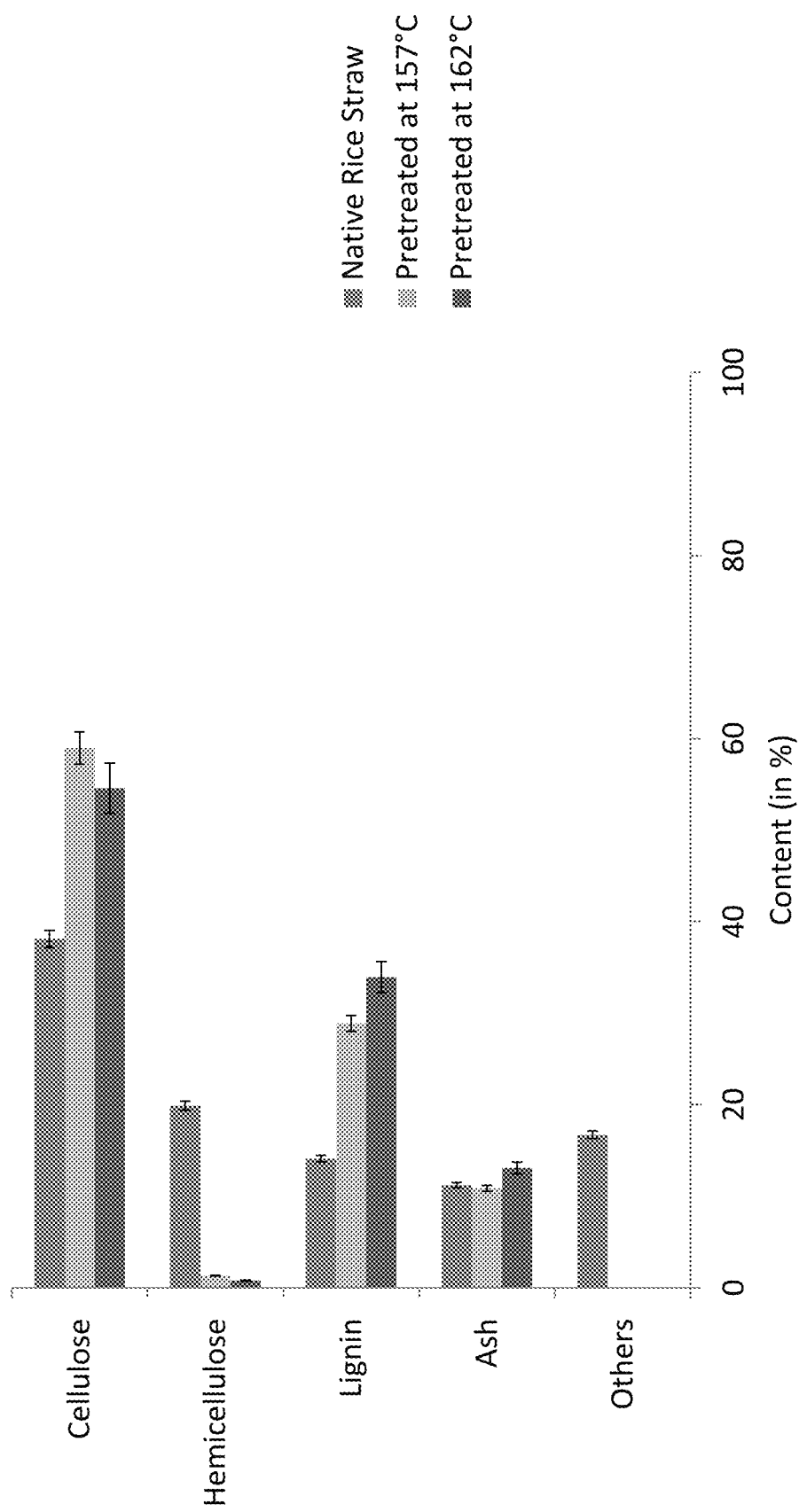
FIG. 2 illustrates composition of native rice straw and dilute acid pretreated rice straw at 157° C. and 162° C.

In another series of experiments, rice straw procured from local market of Faridabad, Haryana, India) was grounded in to 1-2 mm size and pretreated with dilute sulfuric acid in the pilot plant at 0.5% acid concentration at 157° C. for 10 min and 0.25% acid concentration at 162° C. and 10 min residence time. The pretreated slurry was neutralized to a pH of 5 by adding aqueous ammonia and used for enzymatic hydrolysis. The composition of the pretreated rice straw is depicted in the FIG. 2. During dilute acid pretreatment, hemicellulose of the rice straw gets hydrolyzed in to monomeric sugars. Therefore, cellulose and lignin content was apparently increased in the insoluble part of the pretreated rice straw.

Example 2: Evaluation of Petrochemical Waste Stream at Different Enzyme Dosages

Example 2.1: Evaluation of Petrochemical Waste Stream with Dilute Acid Pretreated Wheat Straw (DAWS at 160° C., 0.5% Acid Concentration for 10 Min Residence Time) at Different Enzyme Dosages Enzymatic hydrolysis of pretreated wheat straw was carried out at 10% solid loadings in Erlenmeyer shake flasks at 3-10 FPU/g of solids at 50° C. with 0.5% and 1% of petrochemical waste stream (PW). 2 g DAWS (on dry weight basis), was taken in Erlenmeyer flasks (250 ml) with and without PW and enzyme. A total of 20 ml volume was made up by 0.05M sodium citrate buffer (pH 5.0). Hydrolysis was carried out for 48 h in an incubator shaker at 50° C. and 200 rpm.

Aliquots were withdrawn after 24 hours and 48 hours, centrifuged and supernatants were analyzed for sugars by HPLC equipped with a BioRAD HPX AMINEX column and a refractive index detector (RID). Hydrolysis yield, total theoretical sugars and % increase in yield were calculated as:

Hydrolysis yield (%)=Total sugars(Cellobiose+Glucose+Xylose+Arabinose)produced during hydrolysis*100/Total theoretical sugars present in pretreated biomass   (1)

Total theoretical sugars=Total cellulose and hemicellulose(as determined by composition analysis) *1.111   (2)

% increase in yield=(Hydrolysis yield with surfactant−Hydrolysis yield in control)*100/Hydrolysis yield in control   (3)

Effect of PW supplementation during enzymatic hydrolysis of DAWS was evaluated with 0.5% and 1% of PW with 3-10 FPU of enzyme dosage (FIG. 3). Results of this experiment showed that although hydrolysis of DAWS increased with increasing enzyme dosages but, this increase in hydrolysis yield was not linearly proportional to the enzyme dosage. For DAWS, when PW was added at 0.5% (w/w biomass) concentration, 15.1% and 17.8% increase in hydrolysis was observed at 3 FPU enzyme dosage, and 17.2% and 13.8% increase in hydrolysis was observed at 5 FPU after 24 hours and 48 hours respectively. The increase in hydrolysis was 20.4% and 22.3% at 3 FPU, and 19.2% and 17% at 5 FPU after 24 hours and 48 hours respectively when PW was added at 1% (w/w biomass) concentration.

Results suggest that 0.5% (w/w biomass) of PW at 5 FPU is sufficient to achieve 63% of hydrolysis after 24 hours. However, without PW similar (63%) hydrolysis yield was found at 7 FPU, thus PW has reduced about two FPUs to achieve the same hydrolysis yield. Similarly, the hydrolysis was about equal (~57%) when enzyme was added at a dose of 5 FPU and when enzyme was added at only 3 FPU with 0.5% (w/w biomass) of PW, again indicating a benefit of two FPUs.

Example 2.2: Evaluation of Petrochemical Waste Stream with Steam Pretreated Wheat Straw (SEWS at 160° C., 0.5% Acid Concentration for 10 Min Residence Time) at Different Enzyme Dosages Effect of petrochemical waste stream has also been evaluated with steam pretreated wheat straw at 10% solid loadings, 3-10 FPU/g of solids at 50° C. with 0.5% and 1% (w/w biomass) of petrochemical waste stream (PW) (FIG. 4). Results showed that wheat straw hydrolysis increased significantly by increasing the PW dosage from 0.5% to 1%. When PW was added at 0.5% concentration, 18.8% and 20.8% increase was observed in hydrolysis at 3 FPU enzyme dosage, and 19.9% and 15% increase in hydrolysis was observed at 5 FPU after 24 hours and 48 hours respectively. Similarly, the increase was 21.1% and 24.6% at 3 FPU, and 21.1% and 16.1% at 5 FPU after 24 hours and 48 hours respectively when PW was added at 1% concentration.

Results have shown that hydrolysis yield did not increase in linear fashion with increasing enzyme dosages. Approximately, 49.3%, 60.8%, 70.5% and 82.3% hydrolysis was found at 3, 5, 7 and 10 FPU/g of biomass. By supplementing 0.5% (w/w biomass) of PW with 5 FPU, the hydrolysis equivalent to that achieved at 7 FPU was obtained (i.e., 70%). Results also suggested that 3 FPU is sufficient to achieve 60% hydrolysis if supplemented with 0.5% (w/w biomass) of PW. Therefore, PW could save a minimum of 2 FPU by giving the same hydrolysis yield.

Example 3: Free Protein (%) During Hydrolysis of DAWS and SEWS with and without 0.5% and 1% Petrochemical Waste Stream (PW) at 3 FPU Enzyme Dosage and 10% Solid Loadings A decrease in enzyme adsorption indicates more of free protein to carry out hydrolysis. To monitor the enzyme adsorption with and without PW, free protein was monitored after 24 hours and 48 hours by Bradford method (Bradford, 1976) during enzymatic hydrolysis. Free protein (%) was calculated as protein in sample (mg/ml) divided by total protein added (mg/ml) and multiplied by 100.

The free protein increased from 52 to 59 when 0.5% (w/w biomass) PW was added to DAWS along with 3 FPU of enzyme (FIG. 5). When 1% (w/w biomass) PW was added it increased further to 62% after 48 hours. However, higher amount of free protein was present during enzymatic hydrolysis of SEWS (53% after 24 h and 66% after 48 h) as compared to DAWS. In presence of PW, much higher amount of free protein was observed (80% and 82% respectively at 0.5% and 1% (w/w biomass) PW dosage after 48 hours). The results clearly showed that enzyme-lignin binding reduced in the presence of PW. Availability of enhanced amount of free enzymes in presence of the PW, projects the interesting possibility of re-use of enzymes after hydrolysis.

Example 4: Characterization of Petrochemical Waste Stream and its Comparative Evaluation with Pure Constituents The constituents of PW stream were identified by gas chromatography (GC) and Inductively Coupled Argon Plasma Emission Spectrometer (ICAP). Results showed that PW predominantly contains TEG (42.7%) followed by 27% of TTEG and DEG 0.5% and 1.3% of other higher molecular weight ethylene glycols and some metals (major being Fe, Na, Cr, B and Mn). A synthetic formulation was developed based on this and hydrolysis was performed at 3 FPU/g of DAWS and SEWS at 10% solid loadings. At first, all the constituents were screened individually, and then various combinations of the chosen constituents were checked for improving the process. Ethylene glycols and PW were added at 0.5% dosage while metals (as salts) were added as similar concentrations as found in native PW formulation by ICAP.

Figure 6A:
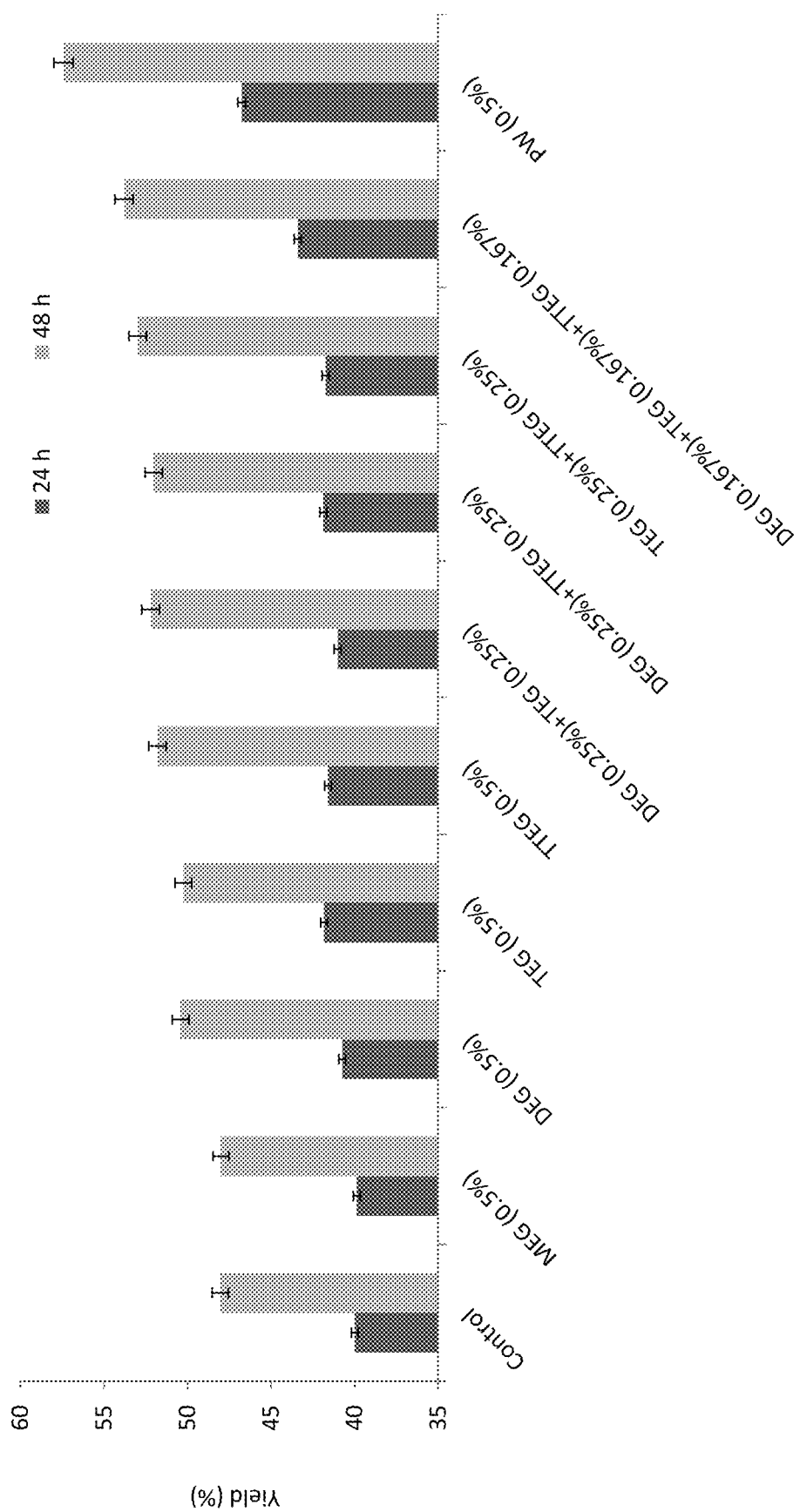
Figure 6B:
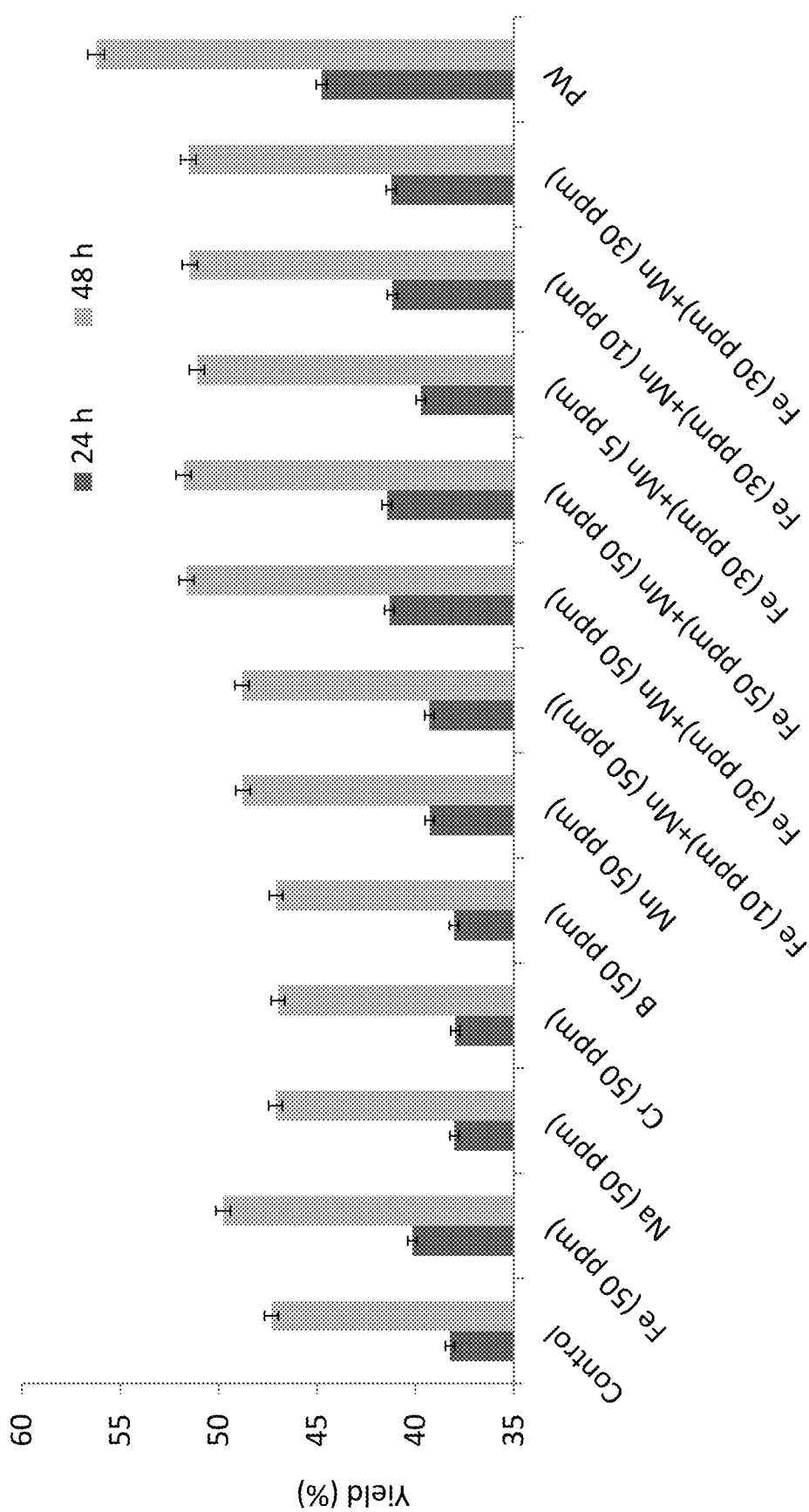
Figure 6D:
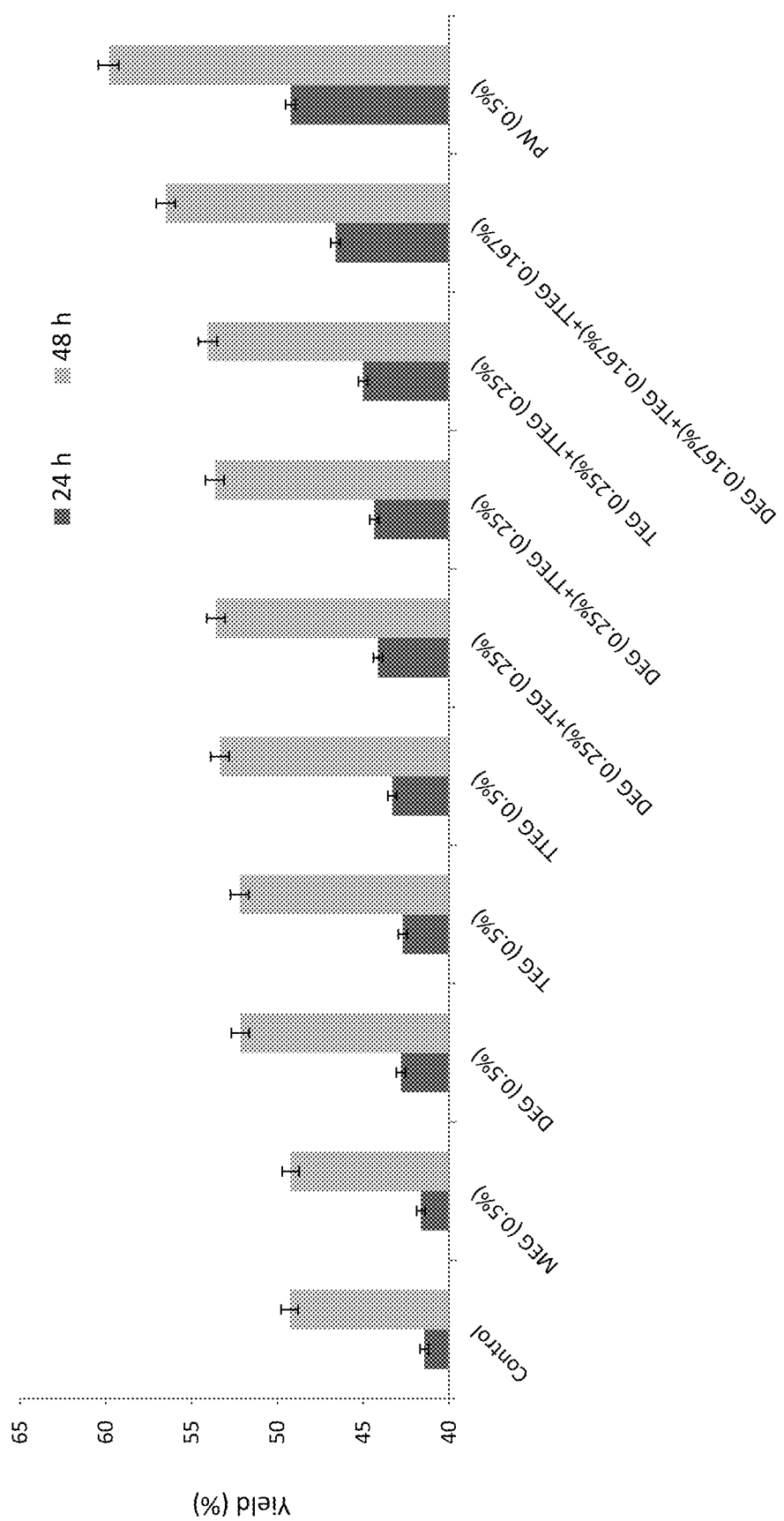

Ethylene glycols namely DEG, TEG, TTEG improved the hydrolysis of both, the DAWS and the SEWS marginally when added at 0.5% (w/w biomass) concentration. Further, the combination of these three (DEG, TEG, TTEG), each added at 0.167% (w/w biomass) substantially improved the yield (FIGS. 6a and 6d). Similarly, a study was done using individual metal ions and their combinations at a concentration of 50 ppm. When added individually, the metals Fe and Mn, shown a positive effect on the yield. No significant effect on hydrolysis yield was observed in the presence of Na, Cr and B. Further, a combination of Fe (30 ppm) and Mn (10 ppm) significantly improved the process.

Metal ions play important roles in the biological function of many enzymes. The various modes of metal-protein interaction include metal-ligand, and enzyme-bridge complexes. Metals can serve as electron donors or acceptors, Lewis acids or structural regulators. Both Fe and Mn are known to stably bound to the enzyme in the catalysis of redox reactions. The control of the reactivity of redox-active metal ions may involve their association with organic cofactors to form stable units. Metals also interact with lignin and reduce its hydrophobicity and lower the non-productive enzyme binding.

Later, a formulation (prepared using the chosen ethylene glycols and metals at optimized concentrations) was tested to improve the hydrolysis of DAWS and SEWS. Results showed that a mixture of identified components (0.167% DEG, 0.167% TEG, 0.167% TTEG, 30 ppm Fe, and 10 ppm Mn) performed synergistically and improved hydrolysis to a greater extent to the same extent as PW.

The combination of DEG, TEG, TTEG (each at 0.167% w/w biomass) improved the hydrolysis of DAWS by 8.5% after 24 hours and 12% after 48 hours as compared to the control after 24 hours and 48 hours (FIG. 6a). While combination of Fe (30 ppm) and Mn (10 ppm) enhanced the hydrolysis by 7.8% after 24 hours and 8.94% after 48 hours (FIG. 6b). But, when all the five components were added together, a synergism was found among these and the hydrolysis increased almost at the same proportion as by PW (i.e., 17% after 24 hours and 19% after 48 hours) (FIG. 6c).

Figure 6E:
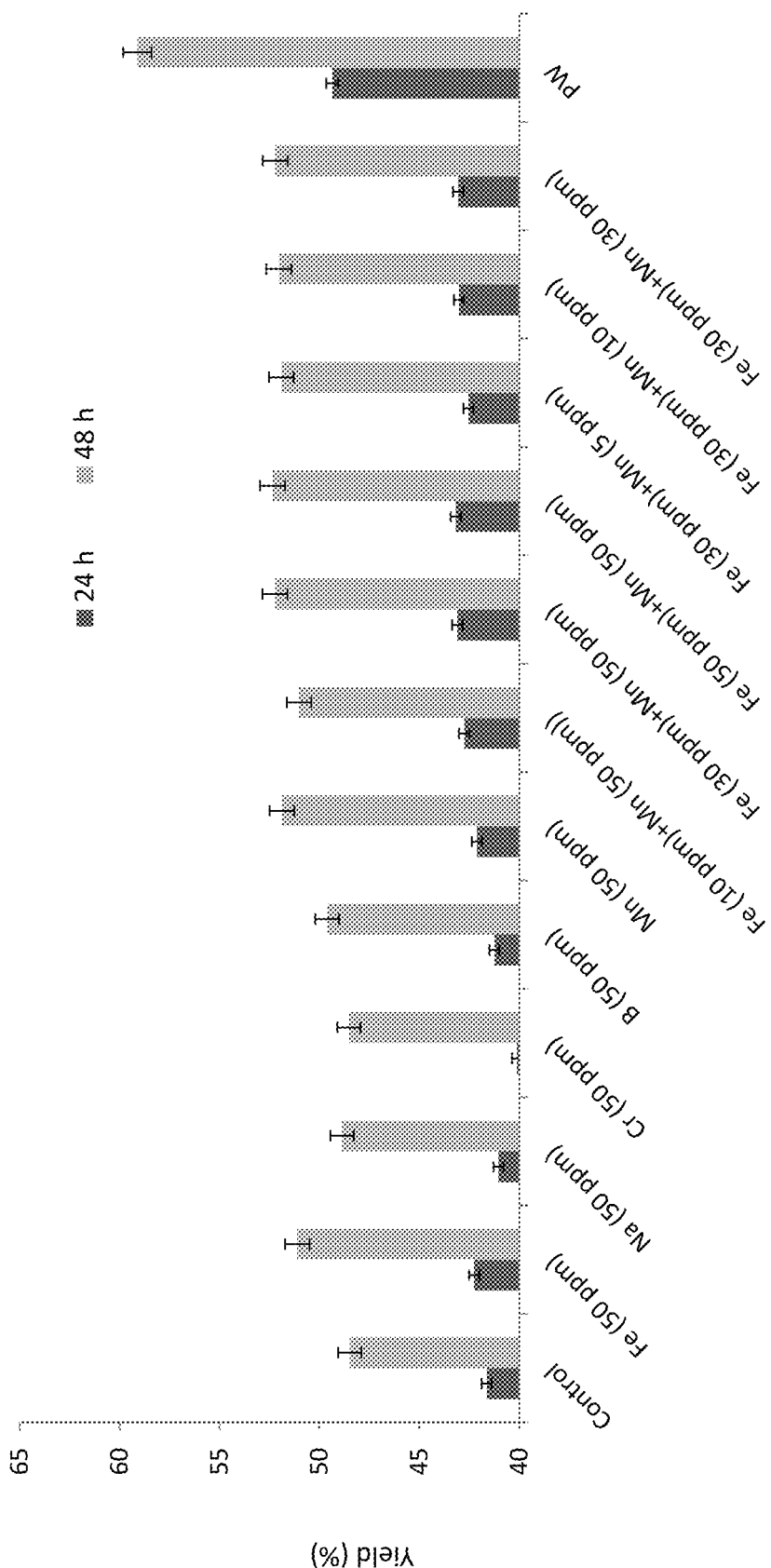

In case of SEWS, the hydrolysis increased by 12.4% after 24 hours and 14.6% after 48 hours as compared to the control when a combination of DEG, TEG, TTEG (each at 0.167% w/w biomass) was added (FIG. 6d). A minor improvement of 3.3% after 24 hours and 7.3% after 48 hours was observed with a combination of Fe (30 ppm) and Mn (10 ppm) on SEWS hydrolysis (FIG. 6e). A strong synergism was observed and the hydrolysis increased almost at the same proportion as by PW (i.e., 19% after 24 hours and 21% after 48 hours) (FIG. 6f).

Example 5: Evaluation of PW on Pretreated Rice Straw at Higher Solid Loadings

Effect of PW was assessed on hydrolysis of rice straw pretreated at 162° C. with 1% dilute $H_2SO_4$ for 10 minutes. Hydrolysis was performed in presence of PW (at 0.5% and 1% w/w of biomass) at 10% and 30% solid loadings and 3-10 FPU/g of biomass in a 2.5 L stirred tank reactors for improved hydrolysis (FIG. 7).

It was found that hydrolysis decreased at higher solid loadings. About 69%, 76%, 84% and 89% hydrolysis was found at 10% solid loading while hydrolysis was 62%, 69%, 76% and 83% at 30% solid loading and at 3, 5, 7 and 10 FPU/g of biomass.

At 10% solid loading, 0.5% (w/w biomass) of PW at 3 FPU was sufficient to achieve 78% hydrolysis after 48 hours. However, without PW almost equal hydrolysis yield (76%) was found at 5 FPU, thus PW has reduced about two FPUs to achieve the same hydrolysis yield. The hydrolysis was almost equal (84%) when enzyme was added at a dose of 7 FPU and when enzyme was added at only 5 FPU with 0.5% (w/w biomass) of PW, indicating a benefit of two FPUs. Similarly, the hydrolysis was almost equal (87-88%) when enzyme was added at a dose of 10 FPU, and when enzyme was added at only 5 FPU with 1% (w/w biomass) of PW, indicating a benefit of three FPUs.

Supplementation with PW had more impact at higher solid loadings (30%) as compared to lower solid loadings (10%) yielding much higher hydrolysis at low enzyme dosages. By supplementing 0.5% (w/w biomass) of PW with 3 FPU, the hydrolysis equivalent to that achieved at 7 FPU was obtained (i.e., 77-78%). Results also suggested that 5 FPU is sufficient to achieve >87% hydrolysis if supplemented with 1% (w/w biomass) of PW which otherwise require about 10 FPU enzyme. Therefore, PW could save a minimum of 5 FPU giving the same hydrolysis yield.

Technical Advancements of the Invention

The present invention discloses following technical advancements, including but not limited to:

Present invention additive works well with high solid loadings (10% to 30%) contrary to prior-art documents where hydrolysis at very low solid loadings (1% to 5%) is applicable.

Present invention utilizes a waste stream from petrochemical unit of refinery in very low concentrations (0.5% to 10% of biomass) for improving the pretreated biomass hydrolysis to produce fermentable sugars.

The waste stream components (DEG, TEG, TTEG, Fe and Mn) in the present invention acts synergistically to improve the pretreated biomass hydrolysis.

The waste stream reduces the non-productive enzyme lignin binding, and enhances the availability of free enzyme for holocellulose hydrolysis.

The utilization of petrochemical waste stream for enhancing the pretreated biomass hydrolysis is a sustainable approach for reducing the enzyme dosage in an economically desirable and profitable manner.

The invention claimed is:

1. A method for production of fermentable sugars from lignocellulosic biomass, comprising:
    a) feeding a grounded lignocellulosic biomass feedstock into a pretreatment reactor system for dilute acid impregnation at room temperature or at a temperature ranging from 50-100° C. for a period 5-60 minutes to render it acid-soaked;
    b) removing 40% 70% acid from said acid-soaked biomass by pressing in a hydraulic press to form a pressed biomass;
    c) feeding said pressed biomass to a plug mill using feed hopper with feed rate of 8-12 kg/hour for conversion into solid plug(s) of the biomass;
    d) treating said solid plug(s) with dilute acid in an amount of 0.02 to 3% w/w of the biomass having pH 1-3 at 120-200° C. for a residence time in the range of 8-12 minutes for conversion into biomass slurry;
    e) centrifuging said biomass slurry for separating solids and liquids, followed by washing solids to a pH of 7.0; and
    f) hydrolyzing said solids with an additive and enzyme for 40-50 hours in an incubator shaker at 45-55° C. having speed of 180-220 rpm to obtain fermentable sugars.

2. The method as claimed in claim 1, wherein the dilute acid used in the pretreatment step is selected from the group consisting of sulphuric acid, hydrochloric acid, acetic acid and phosphoric acid.

3. The method as claimed in claim 1, wherein the additive is a petrochemical waste.

4. The method as claimed in claim 3, wherein the petrochemical waste comprises one or more ethylene glycol oligomer(s) and one or more metal(s).

5. The method as claimed in claim 4, wherein the ethylene glycol oligomer is selected from the group consisting of monoethylene glycol (MEG) present in an amount ranging from 0.0-0.5%, diethylene glycol (DEG) present in an amount ranging from 0.5-30.0%, triethylene glycol (TEG) present in an amount ranging from 40.0-50.0%, and tetraethylene glycol (TTEG) present in an amount ranging from 25-50%.

6. The method as claimed in claim 4, wherein the metal is selected from the group consisting of iron (Fe) in an amount of 0.58%, sodium (Na) in an amount of 0.02%, Chromium (Cr) in an amount of 0.015%, Boron (B) in an amount of 0.012% and manganese (Mn) in an amount of 0.0078%.

7. The method as claimed in claim 4, wherein the petrochemical waste is for production of fermentable sugars from lignocellulosic biomass.

\* \* \* \* \*